(12) United States Patent
Higley

(10) Patent No.: US 6,812,325 B2
(45) Date of Patent: Nov. 2, 2004

(54) POLYAMINES AND POLYMERS MADE THEREWITH

(75) Inventor: David P. Higley, Wilmington, DE (US)

(73) Assignee: Invista North America S.AR.L., Wilmington, DE (US)

( * ) Notice: Subject to any disclaimer, the term of this patent is extended or adjusted under 35 U.S.C. 154(b) by 0 days.

(21) Appl. No.: 10/455,883

(22) Filed: Jun. 6, 2003

(65) Prior Publication Data

US 2003/0208031 A1 Nov. 6, 2003

Related U.S. Application Data

(62) Division of application No. 09/938,696, filed on Aug. 24, 2001, now Pat. No. 6,713,653.

(51) Int. Cl.$^7$ .............................................. C08G 78/02
(52) U.S. Cl. ...................... 528/337; 528/420; 528/432; 528/435
(58) Field of Search ................................ 528/337, 335, 528/339, 342

(56) References Cited

U.S. PATENT DOCUMENTS

| | | |
|---|---|---|
| 3,305,603 A | 2/1967 | McIntyre et al. |
| 3,555,115 A | 1/1971 | Bottomley et al. |
| 3,867,478 A | 2/1975 | Chimura et al. |
| 3,901,853 A | 8/1975 | Tanikella |
| 3,932,126 A | 1/1976 | Jilla |
| 4,001,189 A | 1/1977 | Tanikella et al. |
| 4,001,190 A | 1/1977 | Tanikella et al. |
| 4,145,473 A | 3/1979 | Samuelson et al. |
| 5,000,792 A | 3/1991 | Ohta et al. |
| 5,068,283 A | 11/1991 | Ohmae et al. |
| 5,322,923 A | 6/1994 | Lahary et al. |
| 5,393,849 A | 2/1995 | Srinivasan et al. |
| 6,277,289 B1 | 8/2001 | Kurian et al. |
| 6,331,264 B1 * | 12/2001 | Kurian et al. .......... 264/172.17 |
| 6,576,340 B1 | 6/2003 | Sun et al. |

FOREIGN PATENT DOCUMENTS

| | | |
|---|---|---|
| CA | 974340 | 9/1975 |
| CA | 1028347 | 3/1978 |
| DE | 2233273 | 1/1973 |
| GB | 1373858 | 11/1974 |
| JP | 1972-32184 | 11/1972 |
| JP | 05-105754 A | 4/1993 |
| JP | 95053699 A | 2/1995 |
| WO | WO 00/58393 | 10/2000 |
| WO | WO 01/24693 A1 | 4/2001 |
| WO | WO 01/34693 A2 | 5/2001 |

OTHER PUBLICATIONS

U.S. patent application Ser. No. 09/505,785, filed Feb. 17, 2000. (Issue Fee Mailed Oct. 12, 2001).
U.S. patent application Ser. No. 09/708,209, filed Nov. 8, 2000.
International Search Report dated Dec. 20, 2002.
English Abstract JP 05 105754A (Mitsubishi Chem Ind) Apr. 27, 1993, "Aromatic Polyamides" (XP–002222909).
M. L. Bolognesi et al.; "Universal Template Approach to Drug Design: Polyamines as Selective Muscarinic Receptor Antagonists"; 41 J. Med. Chem. pp. 4150–60(1998) (XP–002222908).
Database Crossfire Beilstein Online!; Beilstein Institut zur Forderung der Chemischen Wissenschaften, Frankfurt am Main, DE; Chem. Pharm. Bull. vol. 32, No. 9, pp. 3428–3435 (1984) (XP–002222910).
K. Samejima, et al., "Syntheses of N–Enriched Polyamines", Chem. Pharm. Bull. vol. 32, No. 9, pp. 3428–3435 (1984).
Written Opinion dated Apr. 24, 2003.

* cited by examiner

Primary Examiner—Samuel Barts

(57) ABSTRACT

A polyamine having the formula:

$$H_2N-A[NR-B]_aNH_2$$

or salt thereof, wherein A and B, which may be the same or different, are selected from aliphatic or aromatic substituents provided that at least four carbon atoms separate any two nitrogen groups, R is an aliphatic or aromatic group, and a is 2 to 5. In addition, a polymer having the formula:

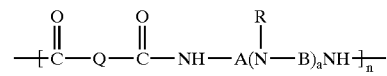

or salt thereof, wherein A, B and Q, which may be the same or different, are selected from aliphatic or aromatic substituents provided that at least four carbon atoms separate any two nitrogen groups, R is an aliphatic or aromatic group, a is greater than 1 to about 5, and n is 3 to about 1,000. The polymers are useful for improving acid-dyeability of polymer compositions, fibers, fabrics, films and other articles.

5 Claims, No Drawings

POLYAMINES AND POLYMERS MADE THEREWITH

PRIORITY

This application claims priority from and is a divisional of U.S. patent application Ser. No. 09/938,696, filed Aug. 24, 2001, now U.S. Pat. No. 6,713,653 incorporated herein by reference.

FIELD OF THE INVENTION

This invention relates to polyamines and polymers made therewith suitable for use in manufacturing fibers, fabrics, films and other useful articles, and to the articles and methods of making such compositions and articles. This invention also relates to processes for preparing the polyamines and polymers and use thereof, including acid-dyeable polymer compositions made with the polymers.

BACKGROUND OF THE INVENTION

Polyesters, especially polyalkylene terephthalates, have excellent physical and chemical properties and have been widely used for resins, films and fibers. In particular, polyester fibers have a high melting point, and can attain high orientation and crystallinity. Accordingly, polyesters have excellent fiber properties such as chemical, heat and light stability, and high strength. However, polyesters, especially polyester fibers and fabrics, are difficult to dye. The molecular structure and the high levels of orientation and crystallinity that impart the desirable properties to the polyester also contribute to a resistance to coloration by dye compounds. Also contributing to the difficulty in dyeing polyester compositions is the characteristic that polyesters do not have dye sites within the polymer chain that are reactive to basic or acid dye compounds.

Nylon polymers are generally dyed more easily than polyesters because of their greater permeability and, in the case of the preferred acid dyes, because the amine end groups in nylon serve as dyesites. However, in many cases these amine-end dyesites are not present at sufficiently high concentration to give the desired depth of dyeing, particularly in fine-denier fibers. Therefore, improvements in the acid dyeability of nylon are desired.

To impart acid dyeability to polyester, it has been proposed to blend polyester with nylon 6 or nylon 6,6 to obtain the benefits of the amine-end dyesites in the resulting polyester/polyamide copolymer composition. The high concentrations of polyamide that may be required to impart dyeability in this polyester/polyamide composition can result in forming polyamide microfibrils, which decrease the physical properties of the polyester/polyamide copolymer and create difficulties in processing.

Co-polymerizing nitrogen containing compounds into polyester chains to improve acid dyeability has been disclosed in, for instance, U.S. Pat. Nos. 3,901,853, 4,001,189 and 4,001,190.

Canadian Patent No. 974,340 discloses acid-dyeable polyester compositions comprising tertiary nitrogen-containing polyamides. Preferred are copolyamides of two or more monomers inclusive of diamines, dicarboxylic acids and aminocarboxylic acids. The tertiary nitrogen component may be derived from piperazine derivatives; HOOC(—CH$_2$)$_n$—NR—(CH$_2$)$_n$—COOH, wherein R can be a group selected from the class consisting of aliphatic (branched or unbranched), cycloaliphatic, aryl or heterocyclic groups; R$_1$—NH—R$_2$—NR$_3$—R$_4$—NHR$_5$, wherein R$_2$ and R$_4$ can be a group selected from aliphatic (branched or unbranched), cycloaliphatic or aryl, R$_1$ and R$_5$ can be a group selected from hydrogen, aliphatic (branched or unbranched), cycloaliphatic or aryl, and R$_3$ is aliphatic (branched or unbranched), cycloaliphatic, aryl or heterocyclic; and cyclic polyamines. Piperazine ring containing polyamides are preferred and all of the examples are directed to these compounds, and to their use with polyethylene terephthalate or polybutylene terephthalate. Piperazine ring containing polyamides, a cyclic compound containing two nitrogens on a single ring, is not sufficiently thermally stable for many applications.

WO 01/34693 (corresponding to co-pending U.S. patent application Ser. No. 09/708,209, filed Aug. 11, 2000 (Docket No. RD-7850)), discloses an acid-dyeable polyester composition made by melt-blending a polyester with a polymeric additive containing a secondary amine salt or a secondary amine, such as made by combining bis(hexamethylene) triamine with a second monomer unit such as a terephthalate. This technology is particularly useful for dyeing fabrics lightly, but adding 3–4 mole % or more of the dye has been found to impact physical properties, particularly tenacity. Tenacity is improved by adding phosphorous acid; however, phosphorous acid leads to instability of pack pressure and may cause spin problems over the long run. In addition, it was not possible to significantly increase the amount of BHMT added using phosphorus acid without spin problems. Therefore, an additive that can provide deep dyeable polyester with acid dyes without such drawbacks is desired.

U.S. Pat. No. 5,000,792 discloses a pigment dispersing agent comprising the polyester reaction product of a polyester having a free carboxyl group, of which the acid value is in the range of from 10 to 60, with an amine compound of the formula: NH$_2$—R$_1$—(NR$_3$)—R$_2$—NH$_2$ wherein R$_1$ and R$_2$ are alkylene radicals which can be the same or different, each containing 2 to 6 carbon atoms, and R$_3$ is a radical of the formula CH$_3$— or C$_2$H$_5$—. The dispersing agent is used to disperse pigments in paints and inks.

All of the aforementioned documents are incorporated herein by reference.

It is desirable to have acid-dyeable nitrogen-containing polymer compositions, particularly polyester and/or nylon compositions, with good physical properties which may be easily processed into fibers, films or other shaped articles and acid-dyed without expensive additives, special solutions, spinning problems, and/or complicated application procedures. It is particularly desirable to be able to deep dye such compositions or shaped articles.

SUMMARY OF THE INVENTION

This invention is directed to a polyamine having the formula:

or salts thereof, wherein A and B, which may be the same or different, are selected from aliphatic or aromatic substituents provided that at least four carbon atoms separate any two nitrogen groups, R is an aliphatic or aromatic group, and a is 2 to 5.

In one preferred embodiment the polyamine is a salt and in another it is not a salt. Preferred salts are acid salts. The polyamine is preferably salinized with phosphorous acid, phosphoric acid, pyrophosphoric acid or phenyl phosphinic acid.

In a preferred embodiment, a is 2.

In a preferred embodiment, the polyamine is:

or salt thereof, wherein x and y, which may be the same or different, are 4 to 10, a is 2 to 5, and R is an alkyl group containing 1 to 8 carbons in a straight or branched chain. In one preferred embodiment, a is 2. In one preferred embodiment the polyamine is a salt and in another it is not a salt.

One preferred polyamine is dimethyltributylenetetramine. One preferred polyamine salt is the phosphorous salt of dimethyltributylenetetramine.

The invention is also directed to polymers having the formula:

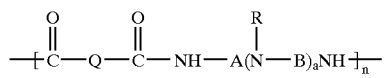

or salts thereof, wherein A, B and Q, which may be the same or different, are selected from aliphatic or aromatic substituents provided that at least four carbon atoms separate any two nitrogen groups, R is an aliphatic or aromatic group, a is greater than 1 to about 5, and n is 3 to about 1,000. Preferably, a is about 2 to about 5.

In one preferred embodiment the polymer is a salt and in another it is not a salt. Preferred salts are acid salts. The polymer is preferably salinized with phosphorous acid, phosphoric acid, pyrophosphoric acid or phenyl phosphinic acid.

Preferably, n is from 3 to about 100, more preferably n is from 3 to about 20.

Preferably, A, B and Q are selected from alkylene substituents containing from 4 to 20 carbons and arylene substituents containing from 6 to 18 carbons. More preferably, R is $C_1$–$C_8$ alkyl, and A and B are $C_4$–$C_8$ alkylene and Q is $C_4$–$C_{10}$ alkylene.

In a preferred embodiment, the polymer is prepared by polymerizing (a) polyamine having the formula:

or salts thereof, wherein x and y, which may be the same or different, are 4 to 10, a is 2 to 5, and R is an alkyl group containing 1 to 8 carbons in a straight or branched chain and (b) aliphatic and aromatic dicarboxylic acids or esters, such as adipic acid, dimethyl adipate, terephthalic acid, dimethyl terephthalate, isophthalic acid, dimethyl isophthalate, naphthalene dicarboxylic acid, dimethyl naphthalene dicarboxylate, or mixtures thereof. Preferred are adipic acid, dimethyl adipate, terephthalic acid, dimethyl terephthalate and mixtures thereof.

The polymers of this invention are useful in preparing acid-dyeable polymer compositions, and in this context, in the following sections of this document are referred to as "polymeric additive(s)" or "polymer compound(s)" and the other polymers, such as nylon or polyester are referred to as the "polymer(s)." Such an acid-dyeable polymer comprises (a) polymer (e.g., nylon or polyester) and (b) the polymeric additive.

Preferred polymers are nylons and polyesters.

Nylon is acid-dyeable and the invention makes it possible to deep-dye nylon or tailor nylons to achieve desired colors. For instance, with this invention it is possible to prepare nylon compositions, fibers and other products which can be dyed to a deep shade. The invention is particularly useful with nylon 6, nylon 4,6, nylon 6,6, nylon 6,10, nylon 6,12, nylon 12,12 and copolymers thereof, and blends thereof.

The composition can be prepared by melt blending the polymer and the polymeric additive. The polymeric additive is added so that the amount of tertiary amine units is effective to promote acid-dyeability. Such compositions are useful in forming fibers, including monocomponent and multicomponent (e.g., bicomponent) fibers. For instance, it may be used as one or both component of a bicomponent fiber comprising poly(ethylene terephthalate) and poly(trimethylene terephthalate) components. The composition can also be used as a film or film layer.

The composition or products made therewith (e.g., fibers or films) can be acid dyed.

DETAILED DESCRIPTION OF THE INVENTION

By "acid-dyeable" it is meant that the composition itself, or fiber, fabric, film or any other article (e.g., shaped articles) made with the composition has an affinity for acid dyes.

The polymer composition preferably comprises either polyesters or nylons, or blends of one or more of these.

Reference to a polymer should be understood to mean a single polymer or blends or mixtures of such a polymer. In other words, "polyester" means one or more polyesters. Thus, for instance, if applicant refers to a composition containing x mole % of a polyester, the composition may comprise x mole % of one polyester or x mole % total of different polyesters. Similarly, "polymeric additive" means one or more polymeric additives.

One preferred class of polymers is polyesters. By "polyester" or "a polyester", applicant is referring to a single polyester, and/or to blends or mixtures of polyesters. The preferred polyesters are polyalkylene terephthalates, polyalkylene naphthalates and polyalkylene isophthalates, and polyalkylene terephthalates are most preferred. More preferred are polyethylene terephthalates, polytrimethylene terephthalates and polytetramethylene terephthalates.

The Mn for the polyester (e.g., polyalkylene terephthalate) is preferably at least about 15,000, more preferably at least about 18,000, and is preferably about 40,000 or less, more preferably about 35,000 or less. The preferred Mn depends on the polyester used.

In the absence of an indication to the contrary, a reference to polyester is intended to include reference to copolyesters. For instance, reference to "polyalkylene terephthalate" is meant also to encompass copolyesters, i.e., polyesters made using 3 or more reactants, each having two ester forming groups. For example, a copoly(ethylene terephthalate) can be used in which the comonomer used to make the copolyester is selected from the group consisting of linear, cyclic, and branched aliphatic dicarboxylic acids having 4 to 12 carbon atoms (for example butanedioic acid, pentanedioic acid, hexanedioic acid, dodecanedioic acid, and 1,4-cyclohexanedicarboxylic acid); aromatic dicarboxylic acids other than terephthalic acid and having 8–14 carbon atoms (for example, isophthalic acid and 2,6-naphthalenedicarboxylic acid); and from linear, cyclic, and branched aliphatic diols having 3–8 carbon atoms (for example, 1,3-propanediol, 1,2-propanediol, 1,4-butanediol, 3-methyl-1,5-pentanediol, 2,2-dimethyl-1,3-propanediol, 2-methyl-1,3-propanediol, and 1,4-cyclohexanediol); and aliphatic and aromatic ether glycols having 4–10 carbon atoms (for example, hydroquinone bis(2-hydroxyethyl) ether, or a poly(ethylene ether) glycol having a molecular weight below about 460, including diethylene ether glycol). The comonomer typically can be present in the copolyester at levels in the range of about 0.5 to about 15 mole %. Isophthalic acid, pentanedioic acid, hexanedioic acid, 1,3-propane diol, and 1,4-butanediol are preferred because they are readily commercially available and inexpensive.

Copoly(trimethylene terephthalate) made from 1,3-propanediol can also be used, in which case the comonomer(s) can be selected from the above list (except the aliphatic diols having 2–8 carbon atoms may be used and ethanediol should replace 1,3-propanediol in the list). The copolyester(s) can contain minor amounts of other comonomers, and such comonomers are usually selected so that they do not have a significant adverse affect on the amount of fiber crimp (in the case of a spontaneously crimpable polyester bicomponent fibers) or on other properties. Very small amounts of trifunctional comonomers, for example, trimellitic acid, can be incorporated for viscosity control.

The most preferred class of polymers are nylons. By "nylon" is meant one or more high molecular weight polyamide(s) which contain an amide repeat linkage in the polymer backbone. They are generally tough, translucent and semicrystalline polymers, typically processed as a melt. There are two main classes of nylon polymers, depending on the regularity of the amide linkages. In one class the formula may be written as:

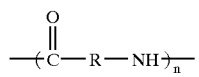

wherein R is preferably $C_5$–$C_8$ alkyl, most preferably $(CH_2)_5$, and wherein n is preferably about 100 to about 180. In the second class, the formula may be written as:

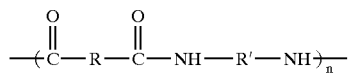

wherein R is preferably $C_4$–$C_{10}$ alkyl, most preferably $(CH_2)_4$, R' is preferably $C_4$–$C_{12}$ alkyl, most preferably $(CH_2)_6$, and wherein n is preferably about 40 to about 80. When the R group has 5 carbons, the first class shown above is generally referred to as nylon 6, and is prepared by ring opening of caprolactam. When the R group has 4 carbons and the R' group has 6 carbons, the second class shown above is generally referred to as nylon 6,6, and is made polymerizing adipic acid and hexamethylene diamine. The invention is useful with all nylons, and preferred are nylon 6, nylon 4,6, nylon 6,6, nylon 6,10, nylon 6,12, nylon 12,12, or their copolymers and blends. Most preferred are nylon 6 and nylon 6,6, or blends thereof.

Nylon 6,6 preferably has an Mn of 10,000 or more, preferably has an Mn of 50,000 or less, preferably has Mw of 20,000 or more, and preferably has a Mw of 50,000 or less.

The polymer compositions can be made using any technique, provided that the composition does not contain substantial amounts of anything that interferes with the goals of the invention.

The polymeric compound, also referred to as the "polymeric additive", has the formula:

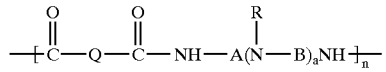

or salts thereof, wherein A, B and Q, which may be the same or different, are selected from aliphatic or aromatic substituents. At least four carbon atoms separate any two of the shown nitrogen groups. R is an aliphatic or aromatic group. R is inclusive of hetero atoms such as nitrogen or oxygen, may be substituted or unsubstituted, and is preferably an alkyl group of 1–8 carbon atoms, and more preferably an alkyl group of 1–4 carbon atoms a is 1 to 5, and n is 3 to about 1,000. Preferably n is up to 100, more preferably up to 20.

It should be understood that the polymeric additive can be polymer consisting essentially of or consisting of the repeating units shown above. Alternatively, it can be a polymer containing polymeric additive units and other polymeric units. Both types of polymeric additives are present in many instances, since when heated most of the polymeric additive will react with polymer or polymer forming compounds to form a new polymeric additive (polymer), while some of the initial polymeric additive remains unreacted. For instance, the composition prior to heating may comprise polyester and polymeric additive, and after heating such a composition may form a combination of polyester, block polymer of reacted polyester and polymeric additive, and unreacted polymeric additive. As another example additive, caprolactam and polymeric additive can form nylon and polymeric additive comprising nylon repeating units and polymeric additive repeating units.

It is preferred that four or more carbon atoms separate any two of the shown nitrogen groups, and most preferred that A and/or B comprise alkylene units having at least four carbons separating the nitrogen atoms, to obtain good thermal stability. The alkylene and arylene units of A and B may be substituted or unsubstituted, straight or branched, etc., as long as the substituent(s) and branches do not substantially interfere with dyeing or other fiber properties (e.g., the chain may contain an ether group).

The number of tertiary amines may vary from unit-to-unit and, therefore, a is an average. Thus, a is greater than 1. Preferably, a is about 2–about 5.

A, B and Q are preferably selected from alkylene substituents containing from 4 to 20 carbons and arylene substituents containing from 6 to 18 carbons.

Q is preferably alkylene or arylene, such as phenylene or naphthylene. Q is preferably $C_4$–$C_{10}$, more preferably $C_4$–$C_8$, alkylene, and is preferably straight chain alkylene.

A and B are preferably $C_4$–$C_{10}$, more preferably $C_4$–$C_8$ alkylene, which are preferably straight chain alkylene.

Preferred for polyester and nylon is R is methyl. Another preferred R for nylon and polyester is isobutyl.

Any suitable synthesis may be used to prepare the polymeric additive. The polymeric additive can be prepared by polymerizing (i) the polyamine or polyamine salt and (b) aliphatic and aromatic dicarboxylic acids or esters (e.g., adipic acid, dimethyl adipate, terephthalic acid, dimethyl terephthalate, isophthalic acid, dimethyl isophthalate, naphthalene dicarboxylic acid, dimethyl naphthalene dicarboxylate or mixtures thereof, etc., preferably adipic acid, dimethyl adipate, terephthalic acid, dimethyl terephthalate and mixtures thereof). The tertiary amine of the polymeric additive can be partly or completely salinized with phosphorous acid, phosphoric acid, pyrophosphoric acid or phenyl phosphinic acid. In a preferred embodiment, the polymeric additive is not a salt.

When preparing the polymeric additive from a dicarboxylic acid the dicarboxylic acid (e.g., terephthalic acid) can be reacted with alcohol to form a diester (e.g., its analogue—dimethyl terephthalate), and the diester is then reacted with the polyamine or polyamine salt to form the polymeric compound. In an alternative embodiment, (a) the polyamine or polyamine salt and (b) dicarboxylic acid are reacted to form the polymeric compound without forming diester intermediate.

Preferably, the polyamine is selected from those having the formula:

or salts thereof, wherein A and B, which may be the same or different, are selected from aliphatic or aromatic substituents provided that at least four carbon atoms separate any two nitrogen groups, R is an aliphatic or aromatic group, and a is 2 to 5.

More preferably, the polyamine is selected from those having the formula:

or salts thereof, wherein x and y, which may be the same or different, are 4 to 10, a is 2 to 5, and R is an alkyl group containing 1 to 10 carbons in a straight or branched chain. Preferably, a is 2 to 4. Preferred polyamines include dimethyltributylenetetraamine (x=y=4, a=2 and R=methyl) or salts thereof, and preferably they are combined with an adipate unit.

Preferred polymeric additives are poly-alkylimino-bisalkylene-adipamides, -terephthalamides, -isophthalamides, or -1,6-naphthalamides, and salts thereof. Most preferred is poly (N,N'-dialkylimino-tri (tetramethylene) adipamide, wherein the alkyl group has one to about four carbon atoms.

The molar ratio of (i) the polyamine containing tertiary amine units and (ii) the one or more other monomer unit is approximately 1:1. It is preferable to add a slight excess on the order of 1 mole %·10 mole % of the polyamine (i) relative to (ii) to promote end capping of the polymeric additive composition with primary amine unit during synthesis. In this embodiment of the invention, the amine groups on the end of the polymeric additive molecule are available to form amide linkages with the polymer component of the composition. An excess of (ii), the one or more other monomer units, may also be used.

The number average molecular weight (Mn) of the polymeric additive (before reaction with polymer units, such as polyester units or nylon units) is preferably at least about 1,000, more preferably at least about 3,000, and most preferably at least about 4,000, and preferably about 10,000 or less, more preferably about 7,000 or less, and most preferably about 5,000 or less. The preferred Mn depends on the polymeric additive used, the balance of the composition and the desired properties.

The polyamine, polymeric additive, composition or products made therewith can be salinized with any acid that stabilizes the amine or protects the amine group until dyeing is carried out. The acid is preferably added to the reaction mixture used to form the polymeric additive. Preferred are inorganic acids such as a phosphorus-containing acids, such as phosphorous acid, phosphoric acid, pyrophosphoric acid or phenyl phosphinic acid, most preferably phosphorous acid. However, when used with polyester compositions, preferably the amount of polymeric additive salinized with phosphorous acid is below 5 mole %, more preferably below 2 mole %, and is preferably above 1 mole % (wherein the mole % is calculated based on the total moles of tertiary amine groups in the polyamine compound).

When the polymeric additive is to be used with nylon, it is preferable to reduce the amount of phosphorous acid added to the reaction mixture for the polymeric additive. Since phosphorous acid is a catalyst for nylon polyamidation, a high level of phosphorous acid may cause a rise in pack pressure during spinning due to a molecular weight increase. With nylon, preferably the amount of polymeric additive salinized with phosphorous acid is below 1 mole % of the total (based on the total moles of tertiary amine groups in the polymeric additive). When used (with nylon), preferably the amount of polymeric additive salinized with phosphorous acid is at least 0.02 mole %, more preferably, at least 0.1 mole %, of the total (based on the total moles of tertiary amine groups in the polymeric additive).

Salinization is normally not necessary, and it is preferred not to salinize the polymeric additive or polymer composition.

The polymer composition of this invention is inclusive of unreacted polymer and polymeric additive.

Preferably the polymer composition is prepared by melt blending the polymeric additive and the polymer. The temperature should be above the melting points of each component but below the lowest decomposition temperature, and accordingly must be adjusted for any particular composition of polymer and polymeric additive. The polymer and polymeric additive may be heated and mixed simultaneously, pre-mixed in a separate apparatus before the heating occurs, or alternately may be heated and then mixed. Further, the polymer composition may be formed and then used, or may be formed during use (e.g., by mixing and heating chips or flakes of polymer and polymer additive in an extruder at a fiber or film manufacturing facility, or by blending molten polymer and polymeric additive in fiber or film manufacture.) Melt blending is preferably carried out at about 200 to about 295° C., most preferably about 260–about 285° C., depending on the polymer. For polytrimethylene terephthalate, the preferred temperatures are about 230 to about 270° C., most preferably about 260° C. For polyethylene terephthalate, the preferred temperatures are about 200 to about 295° C., most preferably about 280–about 290° C. For polybutylene terephthalate, the preferred temperatures are about 200 to about 295° C., most preferably about 250–about 275° C. For nylon 6,6, the preferred temperatures are about 200 to about 295° C., most preferably about 280–about 290° C. For nylon 6, the preferred temperatures are about 200 to about 295° C., most preferably about 260–about 275° C.

As noted previously, the polymer and the polymeric additive can react. Since there is more polymer than polymeric additive, the composition comprises polymeric additive comprising polymer and polymeric additive repeat units and unreacted polymer. In many instances it will also contain polymeric additive that has no units from the polymer.

When polyester and polymeric additive are reacted, the polymer and polymeric additive form a block copolymer by reacting at their ends. By block copolymer, reference is to a polymer formed by the polyester joined to the polymeric additive by a covalent bond. In corresponding nylon compositions, a random copolymer can be formed when the mixing time is long because of transamidation reactions.

The polymeric additive can also be added to the reactants used to form the polymer and, then, when the polymer is formed some of the polymer will contain units derived from polymeric additive. This can result in block or random polymers being formed with polymeric additive as a unit in the chain.

The polymer composition contains an effective amount of polymeric additive containing a tertiary amine unit to promote acid-dyeability. The particular amount of polymeric additive used depends on the polyester or nylon compositions; the polymeric additive used, particularly the nature and amount of tertiary amines; the acid dye used. The preferred amount of polymeric additive can be calculated based on the amount of tertiary amine of the polymeric additive in the composition. Very small amounts of the polymeric additive are needed when it is desired to make minor corrections to the dye depth achieved by the polymer. In such instances the composition can contain as little as about 6 moles tertiary amine/per million grams of the resulting polymer (mpmg). When more than minor changes are desired, the composition preferably contains about 44 or more moles tertiary amine/per million grams of the resulting polymer (mpmg), even more preferably about 88 or more mpmg, and most preferably about 132 mpmg or more, and preferably the composition contains up to about 480 mpmg, more preferably up to about 322 mpmg and most preferably up to 240 mpmg.

It is believed that when linear polymer forming conditions are employed and the polyester (e.g., polyalkylene terephthalate) or nylon and the polymeric additive are mixed and heated to form a composition, the primary amine functional group at the end of the triamine molecule portion of the polymeric additive reacts to form an amide linkage with carboxyl groups of the polyester or nylon, leaving the tertiary amine unit portion of the triamine essentially unreacted and free to form a dye site. Thus, the tertiary amine units become a part of the polymer chain and their presence in the polymer (e.g., polyester or nylon) fiber formed from the acid-dyeable compositions of the invention is permanent and not easily removed by washing, dry cleaning or other processes used to launder fabric articles.

The acid-dyeable polymer composition of the invention typically does not discolor and/or thermally degrade. This is especially advantageous when the polyester or nylon composition is thermally processed, for example, by extrusion from the melt, into shapes such as films, fibers or membranes. The dyed articles are superior in color fastness, brightness, weather resistance, wear resistance and oxidation stability.

The polyester or nylon composition of the invention may be used to produce acid-dyeable shaped articles, including high strength shaped articles. A difficulty is that the use of additives to enhance one property of a polymer, e.g., acid-dyeability, often negatively affects other properties such as processability and strength. However, in accordance with the invention, acid-dyeable, high strength nylon fibers are obtained.

Other additives may be added to the acid-dyeable polyester compositions of this invention to improve strength or facilitate post extrusion processing. For example, hexamethylene diamine and/or polyamides such as nylon 6 or nylon 6,6 may be added in minor amounts (e.g., about 0.5–about 5 mole %) to add strength and processability.

The polymer composition can, if desired, contain various other additives, e.g., antioxidants, delusterants (e.g., $TiO_2$, zinc sulfide or zinc oxide), colorants (e.g., dyes or pigments), stabilizers, flame retardants, fillers (such as calcium carbonate), antimicrobial agents, antistatic agents, optical brightners, extenders, processing aids, viscosity boosters, toning pigments and other functional additives. $TiO_2$ may be added to the polymer or fibers.

The compositions of this invention are useful in fibers, fabrics, films and other useful articles, and methods of making such compositions and articles. By "fibers", reference is made to items recognized in the art as fibers, such as continuous filaments, staple, and other chopped fibers. The fibers may be monocomponent (sometimes also referred to as "homofibers"), or bicomponent or other multicomponent fibers, including sheath-core, eccentric sheath-core, and side-by-side fibers, and yarns made therefrom. Fabrics include knitted, woven and nonwoven fabrics. The compositions may form a film or a film layer, etc.

The acid-dyeable polyester compositions can be used to make acid-dyeable polyester bicomponent fibers, for example, bicomponent fibers comprising poly(ethylene terephthalate) and poly(trimethylene terephthalate) or poly (ethylene terephthalate) and poly(tetramethylene terephthalate). Bicomponent fibers based on poly(ethylene terephthalate) and poly(trimethylene terephthalate) are preferred. The polymeric additive can be incorporated into either or both components. The components can be arranged in a sheath-core, eccentric sheath-core, or side-by-side relationship. When it is desired that the bicomponent fiber be crimpable on drawing, heat-treating, and relaxing to form a stretchable fiber, an eccentric sheath-core or side-by-side relationship can be used; side-by-side is preferred for higher crimp levels. The preferred polyethylene terephthalate/ polytrimethylene terephthalate bicomponent fibers can be manufactured as described in copending U.S. patent application Ser. Nos. 09/758,309 (Docket No. LP4440-CIP1), which is incorporated herein by reference. One or both of the polyesters used in these bicomponent fibers can be copolyesters. Comonomers useful in such copolyesters are described previously. The comonomer can be present in the copolyester at a level in the range of about 0.5 to 15 mole percent.

Acid dyeing is carried out using conventional techniques, such as those used for nylon. The polymer compositions, fibers, films, yarns, fabrics, membranes, etc., may be acid dyed.

The polymer composition, or fibers, films, yarns, fabrics, membranes and other useful shaped articles can be acid dyed to a dye exhaustion of about 30%–about 90% or higher, preferably about 60%–about 95% or higher.

The acid-dyeable polymer compositions according to the present invention contain tertiary amines and are basic compounds. As such, they have a relatively high affinity for acid dyes and can be dyed in a range of colors. For example, the acid dyeable polyester compositions may be spun into fibers and dyed with C.I. Acid Blue 25 (C.I. 62055), C.I. Acid Red 4 (C.I. 14710), C.I. Acid Yellow 40 (C.I. 18950), C.I. Acid Green 25 (C.I. 61570), Tectonic Yellow 2G, Tectilon Red 2B, Tectilon Blue 4R, Lanaset Yellow 2R, Lanaset Red 2B, Lanaset Blue 2R and Irgalan premetallized acid dyes either alone or in combination. (These dyes are available from Ciba Specialty Chemicals Corporation, High Point, N.C. (Ciba).) Acid dye conditions according to the invention are preferably from a pH of 3.5 or more, and a pH of 4.5 or more is especially preferred ranging up to a pH of about 6.5. Of course, lower pH values, e.g., 3.0, may be used if desired.

The invention is further directed to the acid-dyed polymer composition prepared by acid dyeing any of the acid-dyeable polymer compositions described above, and to a process comprising (1) providing the acid-dyeable polyester or nylon composition and (2) acid dyeing the composition, as well as acid-dyed fibers, film, yarn, fabric, membrane, etc.

TESTING METHODS

Intrinsic Viscosity

Intrinsic viscosity (IV) was determined using viscosity measured with a Viscotek Forced Flow Viscometer Y900 (Viscotek Corporation, Houston, Tex.) for the polyester dissolved in 50/50 weight % of trifluoroacetic acid/ methylene chloride at a 0.4 grams/dL concentration at 19° C. following an automated method based on ASTM D 5225-92.

These measured IV values were correlated to IV values measured manually in 60/40 weight % of phenol/1,1,2,2-tetrachloroethane, following ASTM D 4603-96.

DYEING TESTS

A: Tectilon Acid Dyes in the Presence of Carrier

The as-spun yarn was knitted into a sock sample. A 5 gram sock sample was put into a scouring solution containing 2 weight % Merpol HCS nonionic surfactant (DuPont) and 1 weight % acetic acid at 72° C. for 20 minutes. The sample was rinsed and placed into a 100 ml dye-bath containing 1 weight % of either Tectilon yellow 2G, Tectilon red 2B or Tectilon blue 4R and 0.5% Tanalon HIW carrier (Sybron Chemicals, Birmingham, N.J.) at pH 3. The dye bath was heated to 100° C. for 90 minutes. The sample was then rinsed with water and treated with 4% Erional PA solution (Ciba Corporation, Greensboro, N.C.) at pH 4.5–5.0 at 82° C. for 20 minutes for dye fixing. The remaining dye solution was measured in a visible spectrometer to calculate the exhaust.

Tectilon acid dyes were also run without a carrier in an identical manner to that above.

B: Lanaset Acid Dyes in the Absence of Carrier

The as-spun yarn was knitted into sock sample. A 5 gram sock sample was put into a scouring solution containing 2% Merpol HCS and 1% acetic acid at 72° C. for 20 minutes. The sample was rinsed and placed into a 100 ml dye bath containing 2% of either Lanaset Yellow 2R, Lanaset Red 2B, or Lanaset Blue 2R at pH 3. The dye bath was heated to 100° C. for 90 minutes. The sample was then rinsed with water and treated with 4% Erional PA solution at pH 4.5–5.0 at 82° C. for 20 minutes for dye fixing. The remaining dye solution was measured in a visible-range spectrometer to calculate the exhaust.

Tensile Testing of Fiber Yarns

Tensile testing was carried out at 70° F. (21° C.), relative humidity 65%, on an Instron type tensile tester. Yarn samples were twisted 3 turns per inch and were tested at a crosshead speed of 3.6 inches/minute at a gauge length of 6 inches. Five samples were run for each item tested.

EXAMPLES

The following examples are presented for the purpose of illustrating the invention, and are not intended to be limiting. All parts, percentages, etc., are by weight unless otherwise indicated.

Example 1

N,N'-Dimethyl-N,N'-bis(3-cyanopropyl)-1,4-butanediamine

To a mixture of 14.9 g (0.13 mol) of N,N'-dimethyl-1,4-butanediamine (F. Devinsky, I. Lacko, and L. Krasnec, Synthesis (1980), 303–305) and 50 mL of 6M aqueous sodium hydroxide was added with stirring and cooling 39.9 g (0.27 mol) of 4-bromobutyronitrile. The mixture was left standing overnight, then was extracted several times with methylene chloride. Removal of solvent from the combined extracts by rotary evaporation at reduced pressure, followed by molecular distillation at high vacuum, afforded 26.5 g of N,N'-dimethyl-N,N'-bis(3-cyanopropyl)-1,4-butanediamine (0.11 mol, 83% of theory).

Example 2

Dimethyltributylenetetramine

A 26.5-g portion of N,N'-dimethyl-N,N'-bis(3-cyanopropyl)-1,4-butanediamine dissolved in 20 mL of ethanol was hydrogenated over 1.3 g of Raney Cobalt 2724 for eight hours at 75° C. and 900 psig hydrogen pressure. Following removal of catalyst and solvent the product was distilled at ca. 130° C. in a molecular still under high vacuum, affording 24.0 g of dimethyltributylenetetramine.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A polymer having the formula:

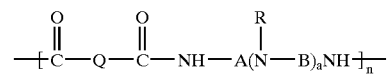

or salt thereof, wherein A is defined as equal to B, and as equal to —(CH2)x— where x=4 to 10; R is defined as a C1 to C8 aliphatic group, straight-chain or branched; Q is phenylene, naphthalene, or a straight-chain C4–C10 alkylene; the value of n is in the range of 10 to 200; and small "a" is 2 to 5.

2. The polymer of claim 1 which is not a salt.

3. The polymer of claim 1 which is a salt.

4. The polymer of claim 3 which is salinized with phosphorous acid, phosphoric acid, pyrophosphoric acid or phenyl phosphinic acid.

5. The polymer of claim 1 prepared by polymerizing (a) polyamine having the formula:

or salts thereof, wherein x and y, which may be the same or different, are 4 to 10, a is 2 to 5, end R is an alkyl group containing 1 to 8 carbons in a straight or branched chain and (b) adipic acid, dimethyl adipate, terephthalic acid, dimethyl terephthalate, isophthalic acid, dimethyl isophthalate, naphthalene dicarboxylic acid, dimethyl naphthalene dicarboxylate or mixtures thereof.

* * * * *